United States Patent
Katsoulis et al.

(10) Patent No.: US 10,081,643 B2
(45) Date of Patent: Sep. 25, 2018

(54) METHOD FOR PRODUCING ARYL-FUNCTIONAL SILANES

(71) Applicant: DOW CORNING CORPORATION, Midland, MI (US)

(72) Inventors: Dimitris Katsoulis, Midland, MI (US); Matthew J. McLaughlin, Midland, MI (US); Robert Morgan, Midland, MI (US); Wendy Sparschu, Bay City, MI (US)

(73) Assignee: Dow Silicones Corporation, Midland, MI (US)

( * ) Notice: Subject to any disclaimer, the term of this patent is extended or adjusted under 35 U.S.C. 154(b) by 0 days.

(21) Appl. No.: 15/508,563

(22) PCT Filed: Nov. 6, 2015

(86) PCT No.: PCT/US2015/059369
§ 371 (c)(1),
(2) Date: Mar. 3, 2017

(87) PCT Pub. No.: WO2016/099690
PCT Pub. Date: Jun. 23, 2016

(65) Prior Publication Data
US 2017/0275306 A1     Sep. 28, 2017

Related U.S. Application Data

(60) Provisional application No. 62/093,473, filed on Dec. 18, 2014.

(51) Int. Cl.
| | |
|---|---|
| *C07F 7/12* | (2006.01) |
| *B01J 23/889* | (2006.01) |
| *B01J 23/86* | (2006.01) |
| *B01J 23/89* | (2006.01) |
| *B01J 23/745* | (2006.01) |
| *B01J 23/75* | (2006.01) |
| *B01J 23/755* | (2006.01) |
| *B01J 37/02* | (2006.01) |
| *B01J 38/42* | (2006.01) |
| *C08G 77/60* | (2006.01) |
| *C01B 33/033* | (2006.01) |
| *B01J 37/18* | (2006.01) |
| *B01J 21/18* | (2006.01) |
| *B01J 23/70* | (2006.01) |

(52) U.S. Cl.
CPC ............. *C07F 7/126* (2013.01); *B01J 23/745* (2013.01); *B01J 23/75* (2013.01); *B01J 23/755* (2013.01); *B01J 23/868* (2013.01); *B01J 23/8892* (2013.01); *B01J 23/8926* (2013.01); *B01J 23/8986* (2013.01); *B01J 37/024* (2013.01); *B01J 37/0236* (2013.01); *B01J 38/42* (2013.01); *C07F 7/12* (2013.01); *C07F 7/122* (2013.01); *C08G 77/60* (2013.01); *B01J 21/18* (2013.01); *B01J 23/70* (2013.01); *B01J 23/8946* (2013.01); *B01J 37/0201* (2013.01); *B01J 37/18* (2013.01); *C01B 33/033* (2013.01)

(58) Field of Classification Search
CPC .......... C07F 7/126; B01J 23/745; B01J 23/75; B01J 23/755; B01J 23/868; B01J 23/8892; B01J 23/8926; B01J 23/8986; B01J 37/0236; B01J 37/024; B01J 38/42; C08G 77/60
USPC ........................................................ 556/466
See application file for complete search history.

(56) References Cited

U.S. PATENT DOCUMENTS

| | | | |
|---|---|---|---|
| 2,403,370 | A | 7/1946 | Hurd |
| 2,406,605 | A | 8/1946 | Hurd |
| 2,888,476 | A | 5/1959 | Little et al. |
| 3,057,686 | A | 10/1962 | Muetterties |
| 4,079,071 | A | 3/1978 | Neale |
| 4,314,908 | A | 2/1982 | Downing et al. |
| 4,474,976 | A * | 10/1984 | Faltynek ................. C07F 7/122 556/481 |
| 4,526,769 | A | 7/1985 | Ingle et al. |
| 4,836,997 | A | 6/1989 | Lepage et al. |

(Continued)

FOREIGN PATENT DOCUMENTS

| | | |
|---|---|---|
| CN | 101624445 A | 1/2010 |
| DE | 3024319 | 1/1982 |

(Continued)

OTHER PUBLICATIONS

Nilsson, M., Science of Synthesis (2002), 4, 247-248.*

(Continued)

*Primary Examiner* — Clinton A Brooks
*Assistant Examiner* — Kofi Adzamli
(74) *Attorney, Agent, or Firm* — Catherine U. Brown

(57) ABSTRACT

A method for preparing a reaction product including an aryl-functional silane includes sequential steps (1) and (2). Step (1) is contacting, under silicon deposition conditions, (A) an ingredient including (I) a halosilane such as silicon tetrahalide and optionally (II) hydrogen ($H_2$); and (B) a metal combination comprising copper (Cu) and at least one other metal, where the at least one other metal is selected from the group consisting of gold (Au), cobalt (Co), chromium (Cr), iron (Fe), magnesium (Mg), manganese (Mn), nickel (Ni), palladium (Pd), and silver (Ag); thereby forming a silicon alloy catalyst comprising Si, Cu and the at least one other metal. Step (2) is contacting the silicon alloy catalyst and (C) a reactant including an aryl halide under silicon etching conditions.

15 Claims, No Drawings

(56) References Cited

U.S. PATENT DOCUMENTS

| | | | |
|---|---|---|---|
| 4,888,435 | A | 12/1989 | Chadwick et al. |
| 4,946,980 | A | 8/1990 | Halm et al. |
| 4,956,326 | A | 9/1990 | Yoneda et al. |
| 4,973,725 | A | 11/1990 | Lewis et al. |
| 5,716,590 | A | 2/1998 | Roewer et al. |
| 6,156,380 | A | 12/2000 | Aramata et al. |
| 6,211,284 | B1 | 4/2001 | Ishikawa et al. |
| 6,326,452 | B1 | 12/2001 | Berrier et al. |
| 6,506,923 | B2 | 1/2003 | Inukai et al. |
| 6,790,749 | B2 | 9/2004 | Takemura et al. |
| 6,887,448 | B2 | 5/2005 | Block et al. |
| 7,208,617 | B2 | 4/2007 | Gammie |
| 7,223,879 | B2 | 5/2007 | Buchwald et al. |
| 7,442,824 | B2 | 10/2008 | Paetzold et al. |
| 7,456,308 | B2 | 11/2008 | Nguyen et al. |
| 7,638,498 | B2 | 12/2009 | Escher et al. |
| 7,716,590 | B1 | 5/2010 | Nathan |
| 8,124,809 | B2 | 2/2012 | Masaoka et al. |
| 8,519,207 | B2 | 8/2013 | Armbruester et al. |
| 8,697,900 | B2 | 4/2014 | Anderson et al. |
| 8,772,525 | B2 | 7/2014 | Katsoulis et al. |
| 8,865,927 | B2 | 10/2014 | Katsoulis et al. |
| 9,422,316 | B2 * | 8/2016 | Dash ............ C07F 7/122 |
| 2005/0074387 | A1 | 4/2005 | Bulan et al. |
| 2005/0220514 | A1 | 10/2005 | Hisakuni |
| 2009/0324477 | A1 | 12/2009 | Mizushima et al. |

FOREIGN PATENT DOCUMENTS

| | | |
|---|---|---|
| DE | 4041644 A1 | 12/1990 |
| DE | 19654154 | 6/1997 |
| JP | S28-000669 | 2/1953 |
| JP | 2009111202 | 5/2009 |
| WO | 2014028417 A2 | 2/2014 |
| WO | 2014062255 A1 | 4/2014 |
| WO | 2014099125 A1 | 6/2014 |
| WO | 2014113124 A1 | 7/2014 |
| WO | 2014149215 A1 | 9/2014 |
| WO | 2014149224 A1 | 9/2015 |

OTHER PUBLICATIONS

Greene et al. Protective Groups in Organic Synthesis, 3rd Ed. Ch. 2 pp. 144-145.*
Bailly et al., RSC Advances, 2011, 1, 1435-1445.*
Hurd, et. al., "The Vapor Phase Alkylation and Hydrogenation of Chlorosilanes", J. Am. Chem. Soc., 1945, 67 (9), pp. 1545-1548.
Eaborn, et al., "Further studies on reactions of organic halides with disilanes catalysed by transition metal complexes", Journal of Organometallic Chemistry, vol. 225, 1982, pp. 331-341.
Golubtsov, et al., "Role of the Products of Partial Chlorination of Silicon in the Formation of Methyltrichlorosilane", Russian Chemical Bulletin, vol. 21, No. 3 (1972), pp. 584-586.
Walter, "Mechanism of the silicide-catalysed hydrodehalogenation of silicon tetrachloride to trichlorosilane", J. Chem. Soc., Faraday Trans., 1996,92, 4605-4608.
Juszczyk, et al., "Transformation of Pd/SiO2 catalysts during high temperature reduction", Department of Catalysis on Metals, Institute of Physical Chemistry, Polish Academy of Sciences, Warsaw, Pol. Catalysis Letters (2002), 78(1-4), 95-98.
Juszczyk, et al., "Transformation of Pd/SiO2 into palladium silicide during reduction at 450° and 500° C.", Institute of Physical Chemistry, Department of Catalysis on Metals, Polish Academy of Sciences, Warsaw, Pol. Journal of Catalysis (2003), 220(2), 299-308.
Lobusevich, et al., "Reactions During Direct Synthesis of Alkylchlorosilanes", vol. 48, No. 11, 1978, pp. 2534-2541.
Moreno-Manas, et. al., "Formation of Carbon-Carbon Bonds under Catalysis by Transition-Metal Nanoparticles", Department of Chemistry, Universitat Autonoma de Barcelona, Barcelona, Spain. Accounts of Chemical Research (2003), 36(8), 638-643.
Acker, et. al., "Reactivity of Intermetallic Compounds: A Solid State Approach to Direct Reactions of Silicon", J. Phys. Chem., 2002, pp. 5105-5117, vol. 106, Freiberg, Germany.
Acker, et. al., "Thermodynamic assessment of the copper catalyzed direct synthesis of methylchlorosilanes", Journal of Organometallic Chemistry, 2008, pp. 2483-2493, vol. 693, Freiberg, Germany.
Banholzer, et. al., "XPS, Auger Stud of Cu3Si and its Reaction With Oxygen", Surface Science, 1986, pp. 125-133, vol. 176, North Holland, Amsterdam.
Roewer, et. al., "Reactivity of Transition Metal Silicides Towards Silicon Tetrachloride/Haloalkanes and Hydrogen", Institute of Inorganic Chemistry, 1998, Trondheim, Norway.
Mulla, et. al., "Reaction of Magnesium Silicide & Silicon Tetrachloride/Trichlorosilane in Presence of Hydrogen", Indian Journal of Chemistry, Sep. 1988, pp. 756-758, vol. 27A.
Beccalli, et. al., "C—C, C—O, C—N Bond Formation on sp2 Carbon by Pd(II)-Catalyzed Reactions Involving Oxidant Agents", Chemical Reviews, 2007, pp. 5318-5365, vol. 107 (11), Washington, DC, United States.
Methivier, et. al., "Characterization and Catalytic Activity for the Methane Total Oxidation", Journal of Catalysis, 1998, pp. 374-382, vol. 173, Villeurbanne Cedex, France.
Srebowata, et. al., "Hydrodechlorination of 1,2-dichloroethane and dichlorodifluoromethane over Ni/C catalysts: The effect of catalyst carbiding", Applied Catalysis A: General 319, 2007, pp. 181-192, Warszawa, Poland.
Tanaka, et. al., "In-situ observation of Pd2Si islands on Si by UHV-TEM/STM", Journal of Crystal Growth, 2002, pp. 254-258, Tsukuba, Japan.
Terao, et. al., "Transition Metal-Catalyzed C—C Bond Formation Reactions Using Alkyl Halides", The Chemical Society of Japan, Bull. Chem. Soc. Jpn., 2006, pp. 663-672, vol. 79, No. 5, Osaka, Japan.
Vijh, et. al., "Discovery of some new stable electrocatalytic materials for the anodic oxidation of hydrazine", Journal of Materials Science Letters, 1993, pp. 113-115, vol. 12, Varennes, Quebec, Canada.
Vijh, et. al., "Electrochemical Activity of Silicides of Some Transition Metals for the Hydrogen Evolution Reaction in Acidic Solutions", Int. J. Hydrogen Energy, 1990, pp. 789-794, vol. 15, No. 11, Great Britain.
Yin, et. a., "Carbon-Carbon Coupling Reactions Catalyzed by Heterogeneous Palladium Catalysts", Chem. Rev. 2007, pp. 133-173, vol. 107, Berlin, Germany.
Song, et al., "Introduction of the Properties, Application and Production of Trichlorosilane", China Chlor-Alkali, Dec. 15, 2002, Series 12, pp. 40-41.
Jun, et. al., "Diproportionation of Chlorotrimethylsilane, Transforming Comprehensive Utilization Research Development", Technology Communications, Mar. 31, 2006, vol. 22, No. 2.
Shengquan, Wu, "Comprehensive Use of Methyltrichlorosilane", Silicone Material, Jan. 22, 2000, vol. 14, Series 1, pp. 23-25.
Jiang, et. al., "Synthesis of Trimethylchlorosilane by [BMIM]Cl—nAlCl3 Ionic Liquids-Catalyzed Redistribution between Methyltrichlorosilane and Low-Boiling Products from the Direct Synthesis of Methylchlorosilanes", Ind. Eng. Chem. Res., Jan. 6, 2011, vol. 50, pp. 1893-1898.

* cited by examiner

METHOD FOR PRODUCING ARYL-FUNCTIONAL SILANES

This application is a U.S. national stage filing under 35 U.S.C. § 371 of PCT Application No. PCT/US15/059369 filed on 6 Nov. 2015, currently pending, which claims the benefit of U.S. Provisional Patent Application No. 62/093473 filed 18 Dec. 2014 under 35 U.S.C. § 119(e). PCT Application No. PCT/US15/059369 and U.S. Provisional Patent Application No. 62/093473 are hereby incorporated by reference.

Methods of preparing halosilanes are known in the art. Typically, halosilanes are produced commercially by the Mueller-Rochow Direct Process, which comprises passing a halide compound over zero-valent silicon ($Si^0$) in the presence of a copper catalyst and various optional promoters. Mixtures of halosilanes are produced by the Direct Process. When an organohalide is used, a mixture of organohalosilanes is produced by the Direct Process.

The typical process for making the $Si^0$ used in the Direct Process consists of the carbothermic reduction of $SiO_2$ in an electric arc furnace. Extremely high temperatures are required to reduce the $SiO_2$, so the process is energy intensive. Consequently, production of $Si^0$ adds costs to the Direct Process for producing halosilanes. Therefore, there is a need for a more economical method of producing halosilanes that avoids or reduces the need of using $S^0$.

Aryl-functional silanes are useful as precursors for the preparation of aryl-functional siloxane polymers and network resins. Aryl-functional resins are used in high temperature coatings and adhesives, and in cookware. The aryl-functional resins are also useful in optoelectronic applications such as for LEDs and optical interconnects. The aryl-functional silanes may further include alkyl groups, which are used to make aryl-, alkyl-functional siloxane polymers. The aryl-, alkyl-functional siloxane polymers are stable at relatively high temperatures and are useful as pump fluids, heat exchange fluids, and base oils for high temperature fluids.

BRIEF SUMMARY OF THE INVENTION

A method for preparing a reaction product comprising an aryl-functional silane is disclosed. The method comprises sequential steps (1) and (2), where:
  step (1) is contacting, under silicon deposition conditions
    (A) an ingredient comprising (I) a halosilane of formula $H_aSiX_{(4-a)}$, where each X is independently a halogen atom and $0 \leq a \leq 1$, and optionally (II) hydrogen ($H_2$); and
    (B) a metal combination comprising copper (Cu) and at least one other metal, where the at least one other metal is selected from the group consisting of gold (Au), cobalt (Co), chromium (Cr), iron (Fe), magnesium (Mg), manganese (Mn), nickel (Ni), palladium (Pd), and silver (Ag);
  thereby forming a silicon alloy catalyst comprising Si, Cu and the at least one other metal; and
  step (2) is contacting the silicon alloy catalyst and (C) a reactant comprising an aryl halide under silicon etching conditions;
thereby forming the reaction product, where the reaction product comprises the aryl-functional silane and a spent catalyst.

DETAILED DESCRIPTION OF THE INVENTION

The Brief Summary of the Invention and the Abstract are hereby incorporated by reference. All ratios, percentages, and other amounts are by weight, unless otherwise indicated. The articles "a", "an", and "the" each refer to one or more, unless otherwise indicated by the context of the specification. The prefix "poly" means more than one. Abbreviations used herein are defined in Table 1, below.

TABLE 1

| Abbreviation | Word |
| --- | --- |
| % | Percent |
| ° C. | degrees Celsius |
| Bu | "Bu" means butyl and includes various structures including nBu, sec-butyl, tBu, and iBu. |
| iBu | Isobutyl |
| nBu | normal butyl |
| tBu | tertiary butyl |
| cm | Centimeter |
| Et | Ethyl |
| FID | flame ionization detector |
| g | Gram |
| GC | gas chromatograph and/or gas chromatography |
| GC-MS | gas chromatograph- mass spectrometer and/or gas chromatography-mass spectrometry |
| hr | Hour |
| kPa | kilopascals absolute |
| Me | Methyl |
| mg | Milligram |
| min | Minutes |
| mL | Milliliters |
| N/A | Not applicable |
| Ph | Phenyl |
| Pr | "Pr" means propyl and includes various structures such as iPr and nPr. |
| iPr | Isopropyl |
| nPr | normal propyl |
| s | Seconds |
| sccm | standard cubic centimeters per minute |
| TCD | thermal conductivity detector |
| uL | Microliter |
| Vi | Vinyl |

"Aryl halide" means a compound having an aromatic hydrocarbyl ring in which one halogen atom is covalently bonded to a carbon atom in the ring (i.e., an aromatic hydrocarbon in which one of the hydrogen atoms directly bonded to a carbon atom in an aromatic ring is replaced by a halogen atom). The aryl halide is exemplified by, but not limited to, chlorobenzene (phenyl chloride), phenyl bromide, and phenyl iodide.

"Metallic" means that the metal has an oxidation number of zero.

"Purging" means to introduce a gas stream into a container to remove unwanted materials.

"Residence time" means the time which a material takes to pass through a reactor system in a continuous process, or the time a material spends in the reactor in a batch process. For example, residence time may refer to the time in step (1) (and when present, step (3)) during which one reactor volume of the metal combination (B) makes contact with the ingredient (A) as the metal combination (B) passes through the reactor in a continuous process or during which the metal combination (B) is placed within the reactor in a batch process. Alternatively, residence time may refer to the time in step (2) (and when present, step (4)) during which one reactor volume of the silicon alloy catalyst makes contact with the reactant (C) as the silicon alloy catalyst passes through the reactor system in a continuous process or during which the silicon alloy catalyst is placed within the reactor in a batch process. Alternatively, residence time may refer to the time for one reactor volume of reactant (C) gas to pass through a reactor charged with the silicon alloy catalyst, e.g., the time for one reactor volume of the reactant (C) to pass through a reactor charged with the silicon alloy catalyst.

For purposes of this application, the term "silicon alloy" means a material of empirical formula $Cu_pAu_qCo_rCr_sFe_t Mg_uMn_vNi_wPd_xAg_ySi_z$, where subscripts p, q, r, s, t, u, v, w, x, y, and z represent the molar amounts of each element present, and p>0, q≥0, r≥0, s≥0, t≥0, u≥0, v≥0, w≥0, x≥0, y≥0, and z>0; with the proviso that at least one of q, r, s, t, u, v, w, x and y is not 0.

"Silicon alloy catalyst" means a solid product that is formed in step (1) of the method described herein, and/or re-formed in step (3) of the method described herein, which is capable of reacting with the aryl halide to form the reaction product.

"Spent catalyst" refers to the silicon alloy catalyst after step (2) (and after step (4), when step (4) is present). The spent catalyst after step (2) (or step (4)) contains an amount of silicon that is less than the amount of silicon in the silicon alloy catalyst after step (1) and before beginning step (2) (or after step (3) and before beginning step (4)). Spent catalyst may, or may not, be exhausted, i.e., spent catalyst may lack silicon or may contain some silicon that may or may not be reactive. Spent catalyst that contains some silicon that is reactive is not exhausted.

"Treating" means to introduce a gas stream into a container to pre-treat a component before contacting the component with another component. Treating includes contacting the metal combination (B) to reduce or otherwise activate the metals before contacting with the ingredient (A) in step (1) of the method and/or to reduce or otherwise activate the silicon alloy catalyst before step (2) of the method.

A method for preparing a reaction product comprising an aryl-functional silane is disclosed. The method comprises sequential steps (1) and (2), where:
  step (1) is contacting, under silicon deposition conditions
    (A) an ingredient comprising (I) a halosilane of formula $H_aSiX_{(4-a)}$, where each X is independently a halogen atom and 0≤a≤1, and optionally (II) hydrogen ($H_2$); and
    (B) a metal combination comprising copper (Cu) and at least one other metal, where the at least one other metal is selected from the group consisting of gold (Au), cobalt (Co), chromium (Cr), iron (Fe), magnesium (Mg), manganese (Mn), nickel (Ni), palladium (Pd), and silver (Ag);
  thereby forming a silicon alloy catalyst comprising Si, Cu and the at least one other metal; and
  step (2) is contacting the silicon alloy catalyst and (C) a reactant comprising an aryl halide under silicon etching conditions;
thereby forming the reaction product, where the reaction product comprises the aryl-functional silane and a spent catalyst; where the method may optionally further comprise sequential steps (3) and (4), where
  step (3) is contacting, under silicon deposition conditions, an additional ingredient comprising (I) an additional halosilane, and optionally (II) additional $H_2$; thereby re-forming the silicon alloy catalyst, and
  step (4) is contacting the silicon alloy catalyst re-formed in step (3) with an additional reactant comprising an additional aryl halide; thereby forming an additional amount of the reaction product, where the reaction product comprises the aryl-functional silane and the spent catalyst; and where the method, when further comprising steps (3) and (4), optionally further comprises step (5), where step (5) is repeating steps (3) and (4) at least one time; and
where the method optionally further comprises step (6), where step (6) is recovering the aryl-functional silane after step (2), and/or when present, step (4), and/or step (5).

In step (1) of the method described herein, a silicon alloy catalyst is formed by contacting an ingredient (A) and a metal combination (B). The ingredient (A) comprises (I) a halosilane and optionally (II) $H_2$. The halosilane has formula $H_aSiX_{(4-a)}$, where each X is independently a halogen atom and subscript a has an average value from 0 to 1. $H_2$ is present, for example, when subscript a=0. The halosilane (I) may be a silicon tetrahalide of formula $SiX_4$, a trihalosilane of formula $HSiX_3$, or a combination thereof. Each X may be independently selected from the group consisting of fluorine (F), chlorine (Cl), bromine (Br), and iodine (I); alternatively, Cl, Br, or I; alternatively Cl, Br, or F; alternatively Cl or Br. Alternatively each X may be Br; alternatively each X may be Cl; alternatively each X may be F; and alternatively each X may be I. The silane may be a tetrahalosilane of formula $SiX_4$, (i.e., where a=0 in the formula above for the halosilane) where each X is as described above. Examples of the tetrahalosilane include, but are not limited to, silicon tetrachloride, silicon tetrabromide, silicon tetraiodide, and silicon tetrafluoride. Alternatively, the silane may be a trihalosilane such as $HSiX_3$, (where a=1 in the formula above for the halosilane) where X is as described above. Examples of trihalosilanes include trichlorosilane ($HSiCl_3$), tribromosilane, and a combination thereof.

The metal combination (B) comprises Cu and at least one other metal selected from Ag, Au, Co, Cr, Fe, Mg, Mn, Ni, and Pd. Alternatively, the at least one other metal may be selected from Ag, Co, Cr, Fe, Mn, Ni, and Pd. Alternatively, the at least one other metal may be selected from Ag, Au, Co, Cr, Mg, Mn, Ni, and Pd. Alternatively, the at least one other metal may be selected from Ag, Co, Cr, Fe, and Mn. Alternatively, the at least one other metal may be Ag. Alternatively, the at least one other metal may be Au. Alternatively, the at least one other metal may be Co. Alternatively, the at least one other metal may be Cr. Alternatively, the at least one other metal may be Fe. Alternatively, the at least one other metal may be Mg. Alternatively, the at least one other metal may be Mn. Alternatively, the at least one other metal may be Ni. Alternatively, the at least one other metal may be Pd. Alternatively, more than one other metal may be present in the metal combination. For example, the metal combination may be Cu, Au, and Mg. Alternatively, the metal combination may be Cu, Ni, and Pd. Alternatively, the metal combination may be Cu, Fe, and Pd. The amount of each metal in the metal combination depends on various factors including the specific metals and temperature selected for step (1). However, the metal combination may contain an amount of Cu up to 90%, alternatively up to 80%, alternatively 20% to 80%, and alternatively 50% of the metal combination, with the balance being one or more of Ag, Au, Co, Cr, Fe, Mg, Mn, Ni, and Pd.

In step (1), the ingredient (A) and the metal combination (B) are contacted under silicon deposition conditions to form a silicon alloy catalyst, i.e., the ingredient (A) and the metal combination (B) are contacted under conditions so as to deposit silicon, such that a ternary or higher silicon alloy catalyst is formed. The silicon alloy catalyst is typically a mixture comprising two or more silicon alloys that differ in at least one property such as amount of Si present, amount of Cu present, morphology, structure and which other metal and/or metals are present. The exact conditions for step (1) will depend on the at least one other metal selected, however, step (1) may be conducted at a first temperature of 200° C. to 1000° C., alternatively 500° C. to 1000° C., alternatively 600° C. to 900° C., alternatively 650° C. to 850° C., alternatively 700° C. to 800° C., and alternatively 750° C., for a time sufficient to form the silicon alloy catalyst.

The copper and at least one other metal of the metal combination (B) may be provided in any convenient form, such as metallic form, e.g., metallic copper, metallic gold, metallic silver, metallic iron, metallic cobalt, metallic chromium, metallic nickel, and metallic palladium. The metallic forms may be mixtures of particles or alloys. Alternatively, metal salts, including, but not limited to, halide, acetate, nitrate, and carboxylate salts of Cu, and one or more of Ag, Au, Co, Cr, Fe, Mg, Mn, Ni, and Pd, may be mixed in desired proportions and then reduced with hydrogen at elevated temperature, typically >300° C., before step (1). Examples of suitable metal salts, which are commercially available, include $CuCl_2 \cdot 2H_2O$, $FeCl_3 \cdot 6H_2O$, $NiCl_2 \cdot 6H_2O$, $PdCl_2$, $CoCl_2$, $Cu(NO_3)_2$, $AgNO_3$, $MnCl_2 \cdot 4H_2O$, $CrCl_3 \cdot 6H_2O$, $AuCl_3$, and $MgCl_2 \cdot 6H_2O$.

The Cu and at least one other metal of the metal combination (B) may optionally be provided on a support. Examples of supports include activated carbon and metal oxides, i.e., oxides of aluminum, titanium, zirconium, and/or silicon. Alternatively, the support may be selected from silica, alumina, and a combination thereof. Alternatively, the support may be alumina. Alternatively, supports that are highly crystalline can be used. Crystalline silica and certain zeolites, such as Zeolite Y or Zeolite Beta products (e.g., which are commercially available as Zeolyst CBV 780 from Zeolyst International), are also examples of supports that can be used. When the metal combination is provided on a support, the supported metal combination may have 5% to 50% of the metal combination with the balance being the support. Alternatively, the supported metal combination may have 10% to 40% metals, alternatively 11% to 30% metals, alternatively 16% to 17% metals, with the balance being the support.

Supported metal combinations may be prepared by any convenient means, such as incipient wetness impregnation or co-precipitation or sol-gel or physical blending of metal oxides. The supported metal combination is prepared by impregnating the support with the precursor. The term "impregnating" means permeating with a wetted, melted, or molten substance throughout all or a portion of a support (e.g., via an incipient wetness technique), preferably to a point where essentially all of a liquid phase substance is adsorbed, producing a liquid-saturated but unagglomerated solid. An illustrative example of a suitable impregnating technique may be found in Example 1 of WO 2011/106194. Alternatively, impregnating may be performed by a depositing-adsorbing technique, such as that found in Example 3 of WO 2011/106194. The precursor may comprise, for example, an aqueous solution of $Cu(NO_3)_2$, $CuCl_2$, or Cu-acetylacetonate and one or more other metal salts described above. The aqueous solution may optionally further comprise an acid, such as HCl. The support may be, for example, alumina, $Fe_2O_3$, $Cr_2O_3$, $SiO_2$, MgO, $La_2O_3$ or $ZrO_2$. Alternatively, the support may be alumina.

Step (1) can be performed in any reactor suitable for the combining of gases and solids. For example, the reactor configuration can be a packed bed, stirred bed, vibrating bed, moving bed, re-circulating bed, or a fluidized bed. When using a re-circulating bed, the silicon alloy catalyst can be circulated from a bed for conducting step (1) to a separate bed for conducting step (2). To facilitate reaction, the reactor should have means to control the temperature of the reaction zone, e.g., the portion of the reactor in which (A) the ingredient and (B) the metal combination contact one another and/or the portion of the reactor in which (A) the ingredient and the silicon alloy catalyst contact one another in step (2).

The pressure at which the ingredient (A) is contacted with the metal combination (B) in step (1) can be sub-atmospheric, atmospheric, or super-atmospheric. For example, the pressure may range from >0 kilopascals absolute (kPa) to 3500 kPa, alternatively 10 kPa to 2100 kPa; alternatively 101 kPa to 2101 kPa; alternatively 101 kPa to 1101 kPa; and alternatively 101 kPa to 900 kPa; and alternatively 201 kPa to 901 kPa.

The mole ratio of hydrogen (II) halosilane (I) in the ingredient (A) contacted with the metal combination (B) in step (1) ranges from 10,000:1 to 0.01:1, alternatively 100:1 to 1:1, alternatively 20:1 to 5:1, alternatively 20:1 to 4:1, alternatively 20:1 to 2:1, alternatively 20:1 to 1:1, alternatively 4:1 to 1:1, and alternatively 3:1 to 1.2:1.

The residence time for the ingredient (A) is sufficient for the ingredient to contact the metal combination (B) and form the silicon alloy catalyst in step (1) and depends on various factors including reactor size and particle size of the metal combination (B). For example, a sufficient residence time for the ingredient (A) may be at least 0.01 s, alternatively at least 0.1 s, alternatively 0.1 s to 10 min, alternatively 0.1 s to 1 min, alternatively 0.5 s to 10 s, alternatively 1 min to 3 min, and alternatively 5 s to 10 s. Alternatively, the residence time for the metal combination (B) to be in contact with the ingredient (A) in step (1) is typically at least 0.1 min; alternatively at least 0.5 minutes; alternatively 0.1 min to 120 min; alternatively 0.5 min to 9 min; alternatively 0.5 min to 6 min. The desired residence time may be achieved by adjusting the flow rate of the $H_2$ and the halosilane, or by adjusting the total reactor volume, or by any combination thereof.

When present, the $H_2$ (II) may be fed to the reactor simultaneously with the halosilane in step (1); however, other methods of combining, such as by separate pulses, are also envisioned. Alternatively, the halosilane (I) and the $H_2$ (II) may be mixed together before feeding to the reactor; alternatively, halosilane (I) and the $H_2$ (II) may be fed into the reactor as separate streams.

The metal combination (B) is used in a sufficient amount. As used herein, a "sufficient amount" of metal combination is enough to form the silicon alloy catalyst, described herein, when halosilane (I) and, when present, the $H_2$ (II) are contacted with the metal combination. For example, a sufficient amount of metal combination may be at least 0.01 mg metal/cm³ of reactor volume; alternatively at least 0.5 mg metal/cm³ of reactor volume; alternatively 1 mg metal/cm³ of reactor volume to maximum bulk density of the metal combination based on the reactor volume, alternatively 1 mg to 5,000 mg metal/cm³ of reactor volume, alternatively 1 mg to 1,000 mg metal/cm³ of reactor volume, and alternatively 1 mg to 900 mg metal/cm³ of reactor volume.

There is no upper limit on the time for which step (1) is conducted. For example, step (1) is usually conducted for at least 0.1 s, alternatively from 1 s to 5 hr, alternatively from 1 min to 1 hr.

Step (1) produces a silicon alloy catalyst comprising an initial weight percent of silicon in the silicon alloy catalyst, based on the total weight of the silicon alloy catalyst, at least 0.1%, alternatively 0.1% to 90%, alternatively 35% to 90%, alternatively 0.1% to 35%, alternatively 1% to 20%, alternatively from 1% to 5%, of silicon. The percentage of silicon in the silicon alloy catalyst can be determined using standard analytical tests. For example, the percentage of silicon may be determined using inductively coupled plasma atomic emission spectroscopy (ICP-AES) or ICP mass spectrometry (ICP-MS). Without wishing to be bound by theory, it is thought that the amount of silicon in the silicon alloy catalyst is less than the amount of silicon in a Direct Process contact mass and the present method provides the benefit of forming a silicon alloy catalyst without the need for $Si^0$ as a starting material.

In step (2) of the method, the silicon alloy catalyst formed in step (1) and a reactant (C) comprising an aryl halide are contacted under silicon etching conditions, i.e., conditions such that the reaction product comprising the aryl-functional silane is formed. Without wishing to be bound by theory, it is thought that in step (2), at least a portion of the silicon alloy catalyst undergoes a compositional change. In step (1), conditions are such that silicon is deposited into the silicon alloy, and in step (2), conditions are such that silicon is etched from the silicon alloy. Step (2) may be performed at a second temperature, which is lower than the first temperature. The second temperature may be 100° C. to 600° C., alternatively 100° C. to 500° C., alternatively 200° C. to 500° C., alternatively 300° C. to 500° C., alternatively 400° C. to 500° C., alternatively 275° C. to 300° C. and alternatively 450° C. to form the reaction product.

The reactant (C) used in step (2) comprises an aryl halide. The aryl halide may have formula $R^1X$, where each X is independently a halogen atom, which may be the same as or different from the halogen atom in the silicon tetrahalide (I) described above. $R^1$ is an aryl group. Examples of aryl groups that can be used for $R^1$ include phenyl, naphthyl, tolyl, xylyl, phenylethyl, phenyl propyl, and phenyl butyl. Alternatively, $R^1$ is selected from phenyl, tolyl and xylyl. Alternatively, $R^1$ is phenyl. Examples of the aryl halide include chlorobenzene, bromobenzene, iodobenzene, and combinations thereof. Alternatively, the aryl halide may be chlorobenzene.

The reactant (C) used in step (2) may optionally further comprise one or more additional components. For example, $H_2$ may be used in addition to the aryl halide. Alternatively, an inert gas may be fed with the aryl halide in step (2). For example, argon or nitrogen, alternatively argon, can be fed in step (2) of the method described herein. Alternatively, an alkyl halide, such as methyl chloride, methyl bromide, methyl iodide, ethyl chloride, ethyl bromide, ethyl iodide, propyl chloride, propyl bromide, propyl iodide, butyl chloride, butyl bromide, or butyl iodide may be added in step (2) in addition to the aryl halide. Alternatively, an hydrogen halide, such as HCl, HBr, or HI; alternatively HCl may be used in addition to the aryl halide in step (2).

The reactors suitable for use in (2) are as described for (1). The same reactor may be used for step (2) as used in step (1); however, separate reactors may also be used. Alternatively, the reactor used in steps (1) and (2) may be a multistage reactor in which step (1) is performed in a first stage and step (2) is performed in a second stage.

The reactant (C) may be contacted with the silicon alloy catalyst by feeding the reactant (C) into a reactor containing the silicon alloy catalyst produced in step (1). The reactor for step (2) may be the same as, or different from the reactor used in step (1).

The residence time for (C) the reactant is sufficient for the reactant to contact the silicon alloy catalyst and form the aryl-functional silane in step (2). For example, a sufficient residence time for the reactant may be at least 0.01 s, alternatively at least 0.1 s, alternatively 0.1 s to 10 min, alternatively 0.1 s to 1 min, alternatively 0.5 s to 10 s, alternatively 1 min to 3 min, and alternatively 5 s to 10 s. Alternatively, the residence time for the silicon alloy catalyst to be in contact with the reactant in step (2) is typically at least 0.1 min; alternatively at least 0.5 minutes; alternatively 0.1 min to 120 min; alternatively 0.5 min to 9 min; alternatively 0.5 min to 6 min. The desired residence time may be achieved by adjusting the flow rate of the reactant, or by adjusting the total reactor volume, or by any combination thereof.

Step (2) is typically conducted until the amount of silicon in the silicon alloy catalyst falls below a predetermined limit, e.g., until the silicon alloy catalyst is spent. For example, step (2) may be conducted until the amount of silicon in the silicon alloy catalyst is below 90%, alternatively 1% to 90%, alternatively 1% to 40%, of its initial weight percent. The initial weight percent of silicon in the silicon alloy catalyst is the weight percent of silicon in the silicon alloy catalyst after step (1) and before beginning step (2). The amount of silicon in the silicon alloy catalyst can be monitored by correlating production of the reaction product of step (2) with the weight percent of silicon in the reactant and then monitoring the reactor effluent or may be determined as described herein. Alternatively, step (2) is conducted until at least 1% of the silicon contributed in step (1) is reacted; alternatively, step (2) is conducted until 1% to 40% of the silicon contributed in step (1) is reacted; alternatively, step (2) is conducted until at least 90% of the silicon contributed in step (1) is reacted; alternatively step (2) is conducted until greater than 95% of the silicon contributed in step (1) is reacted, alternatively step (2) is conducted until greater than 99% of the silicon contributed in step (1) is reacted, and alternatively step (2) is conducted until 99.9% of the silicon contributed in step (1) is reacted. Without wishing to be bound by theory, it is thought that more silicon is deposited in step (1) of the method described herein, and more silicon is removed in step (2) in this method as compared to methods in which only a binary silicon alloy catalyst (i.e., an alloy of silicon and only one other metal in the catalyst) is used with the same ingredients and reactants.

The pressure at which the ingredient comprising hydrogen and the halosilane is contacted with the silicon alloy catalyst in step (2) can be sub-atmospheric, atmospheric, or super-atmospheric. For example, the pressure may range from 0 kPa to 3500 kPa, 10 kPa to 2100 kPa; alternatively 101 kPa to 2101 kPa; alternatively 101 kPa to 1101 kPa; and alternatively 101 kPa to 900 kPa; and alternatively 201 kPa to 901 kPa.

The silicon alloy catalyst is used in a sufficient amount. As used herein, a "sufficient amount" of silicon alloy catalyst is enough catalyst to form the aryl-functional silane described below. For example, a sufficient amount of silicon alloy catalyst may be at least 0.01 mg silicon alloy catalyst/$cm^3$ of reactor volume; alternatively at least 0.5 mg metal/$cm^3$ of reactor volume; alternatively 1 mg silicon alloy catalyst/$cm^3$ of reactor volume to maximum bulk density of the silicon alloy catalyst based on the reactor volume, alternatively 1 mg to 5,000 mg silicon alloy catalyst/$cm^3$ of reactor volume, alternatively 1 mg to 1,000 mg silicon alloy catalyst/$cm^3$ of reactor volume, and alternatively 1 mg to 900 mg silicon alloy catalyst/$cm^3$ of reactor volume.

Steps (1) and (2) of the method are performed sequentially. Alternatively, steps (1) and (2) of the method may be performed separately and sequentially. "Separate" and "separately" each mean that step (1) and step (2) do not overlap or coincide. "Separate" and "separately" refer to either spatially or temporally or both. The terms "sequential" and "sequentially" each mean that one step is performed after a different step in the method (e.g., step (2) is performed after step (1), and when present, step (4) is performed after step (3)) in the method; however, additional steps may be performed between the sequential steps (e.g., between step (1) and step (2) and/or between step (3) and step (4), when steps (3) and (4) are present in the method), as described below. Alternatively, steps (3) and (4) are present and are also performed sequentially; alternatively steps (3) and (4) may be performed separately and sequentially.

The method described herein may optionally further comprise purging and/or treating. Purging and/or treating may be performed at various times during the method. For example, the method described herein may optionally further comprise one or more of the following purging and/or treating steps:

purging and/or treating the metal combination, before contacting the metal combination with the ingredient comprising the halosilane in step (1); and/or purging and/or treating the silicon alloy catalyst, before contacting the silicon alloy catalyst with the reactant comprising the aryl halide in step (2); and/or purging and/or treating, the spent reactant before contacting the spent reactant with the additional ingredient in step (3); and/or purging and/or treating the reactant re-formed in step (3), before contacting the reactant re-formed in step (3) with the additional reactant in step (4); and/or purging and/or treating the additional spent reactant. The purging step comprises introducing a gas stream into the reactor to remove unwanted materials. Unwanted materials in step (2), and when present step (4), may include, for example, $H_2$, $O_2$, $H_2O$ and HX, where X is a halogen atom as defined above Purging may be accomplished with an inert gas, such as argon, nitrogen, or helium or with a reactive gas, such as the halosilane (I) (e.g., silicon tetrachloride), which reacts with moisture thereby removing it. Purging before step (1) may be done to at least partially remove any oxide layer that may be present on a metal in the metal combination. The treating step may comprise introducing a gas stream into the reactor containing the metal combination to pre-treat the metal combination before contacting it with the ingredient (A) in step (1). Alternatively, the treating step may comprise introducing a gas stream into the reactor containing the silicon alloy catalyst to activate and/or reduce it before contacting the silicon alloy catalyst with the aryl halide. Treating may be accomplished with a gas, such as $H_2$ or the aryl halide; alternatively $H_2$. Purging and/or treating may be performed at ambient or elevated temperature, e.g., at least 25° C., alternatively at least 300° C., alternatively 25° C. to 500° C., and alternatively 300° C. to 500° C.

The method may optionally further comprise recovering side products and unreacted ingredients and/or unreacted reactants after each step of this method. For example, a hydrogen halide, such as HCl, may be produced as a side product in step (1). This hydrogen halide may be removed. Unreacted ingredients, such as $SiCl_4$, may be recycled in step (1) or fed to step (2).

In one embodiment, the method further comprises step (3) repeating step (1) by contacting the spent catalyst formed in step (2) with an additional ingredient (A) comprising an additional halosilane and optionally additional $H_2$ under silicon deposition conditions (e.g., at the first temperature of 200° C. to 1000° C.); thereby re-forming the silicon alloy catalyst; and step (4) repeating step (2) by contacting an additional reactant (C) and the silicon alloy catalyst re-formed in step (3) under silicon etching conditions (e.g., at the second temperature from 100° C. to 600° C.), to form additional reaction product. The additional halosilane (I) used in step (3) may be the same as or different from, the halosilane used in step (1), and the additional reactant (C) may be the same as, or different from, the reactant (C) used in step (2), as described above. Step (3) may be performed without introducing an additional amount of ingredient (B). The temperature selected for step (4) is lower than the temperature selected for step (3). Without wishing to be bound by theory, it is thought that use of the silicon alloy catalyst described herein may prevent loss of metal upon repeated cycles (repetitions of steps (3) and (4)).

Without wishing to be bound by theory, it is thought that the method described herein allows for maximizing the number of cycles for repeating steps (3) and (4). The method may optionally further comprise step (5), which is repeating steps (3) and (4) at least 1 time, alternatively from 1 to $10^7$ times, alternatively $10^5$ to $10^7$ times, alternatively from 1 to 1,000 times, alternatively from 1 to 100 times, alternatively 2 to 15 times, and alternatively from 1 to 10 times. Without wishing to be bound by theory, it is thought that in methods in which a noninventive binary metal silicide catalyst (i.e., containing Si, and one other metal, such as copper) is used (instead of the silicon alloy catalyst which contains silicon, copper and at least one other metal, as described herein), the binary metal silicide catalyst may suffer from the drawback of metal loss upon repeated cycles (repetitions of steps (3) and (4)), and that the method described herein may provide higher throughput for each cycle than previous methods in which a binary copper silicide, is used instead of a silicon alloy catalyst described herein.

The method may further comprise pre-heating and gasifying the halosilane (I) by known methods prior to contacting with the metal combination (B) in step (1). The method may further comprise pre-heating and gasifying the aryl halide prior to contacting with the silicon alloy catalyst in step (2).

The method may further comprise step (6), recovering the aryl-functional silane from the reaction product produced. The aryl-functional silane may be recovered by, for example, removing gaseous silicon tetrahalide and any other gases from the reactor followed by isolation of the aryl-functional silane by distillation.

The aryl-functional silane produced by the process described and exemplified above has the formula $R^2_d H_c R^1_b SiX_{(4-b-c-d)}$, where each X is a halogen atom as described above, subscript c has an average value from ≥0 to <4, subscript b has an average value from >0 to 4, subscript d has an average value from 0 to <4, each $R^1$ is an aryl group, and each $R^2$ is independently a hydrocarbyl group selected from alkyl, alkenyl, cycloalkyl, and alkynyl. Alternatively, subscript b has an average value from 1 to 4. Alternatively, subscript c is 0 or 1, subscript d is 0 or 1 and subscript b is 1 to 3. Examples of aryl-functional silanes prepared according to the present method include, but are not limited to, $PhHSiCl_2$, $PhSiCl_3$, $Ph_2SiCl_2$, $Ph_3SiCl$, $PhSiBr_3$, $Ph_2SiBr_2$, $Ph_3SiBr$, $PhHSiBr_2$, $PhSiI_3$, $Ph_2SiI_2$, $PhHSiI_2$, and $Ph_3SiI$. Alternatively, when each X is Cl, then the aryl-functional silanes prepared according to the present method include, but are not limited to, $PhSiCl_3$, $Ph_2SiCl_2$, and $PhHSiCl_2$. Alternatively, when an alkyl halide is included in the reactant in step (2), then the method may produce aryl-, alkyl-functional silanes (i.e., the aryl-functional silane may further comprise an alkyl group). Examples of such aryl-, alkyl-functional silanes may include one or more of PhMeSiCl, PhMeSiCl$_2$, Ph$_2$MeSiCl, PhMeSiBr, PhMeSiBr$_2$, Ph$_2$MeSiBr, PhMeSiI, PhMeSiI$_2$, and Ph$_2$MeSiI; alternatively one or more of PhMeSiCl, PhMeSiCl$_2$, and Ph$_2$MeSiCl.

The method described herein can produce an aryl-functional silane from a halosilane, such as a silicon tetrahalide. Since silicon tetrahalide, such as silicon tetrachloride, is a by-product of other industrial processes and may be produced using less energy than required to produce zero-valent silicon, the method of the invention may be more economical than methods of producing aryl-functional silanes using Si$^0$. The method described herein may also provide a benefit over other chemistries for making aryl-functional silanes, such as Psuedo Friedel Crafts reactions and/or Grignard processes, in that the method described herein produces fewer cyclohexyltrihalosilane impurities. The method described herein may also be performed without the use of organic solvents.

Aryl-functional silanes are useful as precursors for the preparation of aryl-functional siloxane polymers and resins. When aryl-functional silanes may also include alkyl groups (i.e., aryl-, alkyl silanes), these maybe used as precursors for the preparation of and aryl-, alkyl-functional siloxane polymers. The aryl-, alkyl-functional siloxane polymers are stable at relatively high temperatures and are useful as pump fluids, heat exchange fluids, and base oils for high temperature fluids. Aryl-functional siloxane resins are used in high temperature coatings and adhesives, for example, in cookware. The aryl-functional siloxane resins generally have high refractive index, which render them useful in optoelectronic applications. The aryl-functional siloxane resins may be used in optoelectronic applications such as for forming encapsulating materials for optoelectronic components such as LEDs, optoelectronic coatings, and optical interconnects.

EXAMPLES

These examples are intended to illustrate some embodiments of the invention and should not be interpreted as limiting the scope of the invention set forth in the claims. Reference examples should not be deemed to be prior art unless so indicated.

The reaction apparatus used in the examples herein comprised a 4.8 mm inner diameter quartz glass tube in a flow reactor. The reactor tube was heated using a Lindberg/Blue Minimite 2.54 cm tube furnace. Hydrogen gas was delivered via a Brooks Delta mass flow controller and Ar was delivered via Omega FMA 5500 mass flow controller. A stainless steel SiCl$_4$ bubbler was used to introduce SiCl$_4$ into the H$_2$ gas stream. The amount of SiCl$_4$ in the H$_2$ gas stream was adjusted by changing the temperature of the SiCl$_4$ in the bubbler according to calculations using thermodynamic principles. The reactor effluent passed through an actuated 6-way valve from Vici.

The effluent of the reactor containing the reaction product was passed through an actuated 6-way valve (Vici) with constant 100 μL injection loop before being discarded. Samples were taken from the reaction stream by actuating the injection valve and the 100 μL sample passed directly into the injection port of a 6890N Agilent GC for analysis with a split ratio at the injection port of 100:1. The GC contained two Restek DCA columns. One column was connected to a mass spectrometer (Agilent 5975C MSD) for sensitive detection of trace products and positive identification of any products that formed. The other was connected to a thermal conductivity detector for quantification of the compounds observed in the reactor effluent by the MSD. The columns were heated by the GC oven. Flow rate ratios were determined using thermodynamic principles with the flow rates, at standard temperature and pressure, of Hydrogen, Argon, SiCl$_4$, and chlorobenzene.

Reference Example 1

Preparation of Supported Metal Combinations

A copper salt and at least one other metal salt were dissolved in de-ionized H$_2$O. A portion of the resulting solution was added to activated carbon granules. The granules were then placed under vacuum for 30 min. After removing the vacuum, the resulting solid was dried at 80° C. for 2 hr. An additional impregnation was done (solution added to the solid, vacuum pulled, and heated), so that all of the solution had been added to the granules, which were then dried a final time at 120° C. for 15 hours. After drying, the granules were weighed to determine the metal loading. In some sample, hydrochloric acid was added to the metal salt/H$_2$O solution dropwise to fully dissolve the metal salt and then used for impregnation. When HCl was used, it was added dropwise until the metal chloride was dissolved, and the concentration of HCl was 5% to 37%. The supported metal combinations prepared in this manner are described below in Table 2.

TABLE 2

Supported metal combination samples used in the Examples.

| Sample # | Cu—M weight % | Metal Salt | Amount of each Metal Salt | Carbon amount | HCl present? |
| --- | --- | --- | --- | --- | --- |
| 1 | Cu—Ni/C (14.5-13.4% w/w) | CuCl$_2$—2H$_2$O NiCl$_2$—6H$_2$O | 0.837 g 1.168 g | 0.993 g | No |
| 2 | Cu—Ni/C (9.0-4.0% w/w) | CuCl$_2$—2H$_2$O NiCl$_2$—6H$_2$O | 0.464 g 0.220 g | 0.823 g | No |
| 3 | Cu—Fe/C (14.7-12.9% w/w) | CuCl$_2$—2H$_2$O FeCl$_3$—6H$_2$O | 0.853 g 1.358 g | 0.782 g | No |
| 4 | Cu—Fe/C (9.1-3.8% w/w) | CuCl$_2$—2H$_2$O FeCl$_3$—6H$_2$O | 0.469 g 0.247 g | 0.787 g | No |
| 5 | Cu—Pd/C (8.4-14.2% w/w) | CuCl$_2$—2H$_2$O$_2$ PdCl$_2$ | 0.602 g 0.943 g | 1.459 g | Yes |
| 6 | Cu—Pd/C (9.1-5.4% w/w) | CuCl$_2$—2H$_2$O PdCl$_2$ | 0.621 g 0.229 g | 1.157 g | Yes |
| 7 | Cu—Co/C (12.9-12.0% w/w) | CuCl$_2$—2H$_2$O CoCl$_2$ | 0.836 g 0.636 g | 1.530 g | Yes |

TABLE 2-continued

Supported metal combination samples used in the Examples.

| Sample # | Cu—M weight % | Metal Salt | Amount of each Metal Salt | Carbon amount | HCl present? |
|---|---|---|---|---|---|
| 8 | Cu—Cr/C (12.3-10.0% w/w) | $CuCl_2$—$2H_2O$<br>$CrCl_3$—$6H_2O$ | 0.887 g<br>1.382 g | 0.736 g | No |
| 9 | Cu—Mn/C (16.4-14.2% w/w) | $CuCl_2$—$2H_2O$<br>$MnCl_2$—$4H_2O$ | 1.630 g<br>1.336 g | 1.089 g | No |
| 10 | Cu—Ag/C (9.1-5.4% w/w) | Cu(NO3)2<br>AgNO3 | 0.547 g<br>0.134 g | 0.830 g | No |
| 11 | Cu—Ni—Pd/C (6.1-5.6-5.1% w/w) | $CuCl_2$—$2H_2O$<br>$NiCl_2$—$6H_2O$<br>$PdCl_2$ | 0.293 g<br>0.406 g<br>0.152 g | 1.148 g | Yes |
| 12 | Cu—Ni—Pd/C (6.1-5.6-5.1% w/w) | $CuCl_2$—$2H_2O$<br>$NiCl_2$—$6H_2O$<br>$PdCl_2$ | 0.222 g<br>0.308 g<br>0.116 g | 0.868 g | Yes |
| 13 | Cu—Ni—Pd/C (4.2-3.9-1.8% w/w) | $CuCl_2$—$2H_2O$<br>$NiCl_2$—$6H_2O$<br>$PdCl_2$ | 0.116 g<br>0.162 g<br>0.030 g | 0.692 g | Yes |
| 14 | Cu—Ni—Pd/C (5.0-4.7-0.8% w/w) | $CuCl_2$—$2H_2O$<br>$NiCl_2$—$6H_2O$<br>$PdCl_2$ | 0.184 g<br>0.262 g<br>0.019 g | 0.985 g | Yes |
| 15 | Cu—Ni—Pd/C (5.4-5.0-0.5% w/w) | $CuCl_2$—$2H_2O$<br>$NiCl_2$—$6H_2O$<br>PdCl2 | 0.136 g<br>0.187 g<br>0.007 g | 0.671 g | Yes |
| 16 | Cu—Fe—Pd/C (4.9-4.2-4.1% w/w) | $CuCl_2$—$2H_2O$<br>$FeCl_3$—$6H_2O$<br>$PdCl_2$ | 0.225 g<br>0.351 g<br>0.117 g | 0.813 g | Yes |
| 17 | Cu—Au—Mg/C (23.7-1.1-0.5% w/w) | $CuCl_2$—$2H_2O$<br>$AuCl_3$<br>$MgCl_2$—$6H_2O$ | 5.315 g<br>0.139 g<br>0.163 g | 4.330 g | No |

The metal loaded activated carbon was charged into a tube and placed into a flow reactor. Activation and reduction of catalyst was performed by flowing $H_2$ at 100 sccm (controlled via Brooks Delta mass flow controller) into the glass tube containing the catalyst in the reactor at 600° C. for 2 hours. The heating was accomplished using a Lindberg/Blue Minimite 2.54 cm tube furnace.

Reference Example 2

Reaction Procedure for Examples

An activated carbon supported metal combination (0.5 g), prepared as described in Reference Example 1, was treated in $H_2/SiCl_4$ for 30 min at 750° C. by bubbling $H_2$ through a stainless steel $SiCl_4$ bubbler at −4° C. The total flow of $H_2$ and $SiCl_4$ was 109 sccm and the mole ratio of $H_2$ to $SiCl_4$ was 11.25:1. The gas and vapor leaving the bubbler was fed into the tube of the flow reactor containing the supported metal combination to form a silicon alloy catalyst. After 30 minutes the $SiCl_4$ flow was ceased and a hydrogen flow of 100 sccm was maintained while cooling to 400° C. over a period of 20 min to 1 hour. When the reactor reached 400° C., the $H_2$ flow was either decreased or stopped. The PhCl was fed through the reactor with either $H_2$ or Ar at a flow rate of 2 sccm and atmospheric pressure. The reactor effluent was periodically sampled and analyzed by GC-TCD/GC-MS as described above to determine the composition of the reaction product. Next, the PhCl feed was ceased, and the spent catalyst was contacted again with $H_2/SiCl_4$ for 30 min at 750° C. to reform the silicon alloy catalyst. The combined flow rate of $H_2$ and $SiCl_4$ was 109 sccm, and the mole ratio of $H_2$ to $SiCl_4$ was 11.25:1. After the silicon alloy catalyst was reformed, it was cooled to 400° C. under $H_2$, again, and PhCl was contacted with the reformed silicon alloy as described above. This cycle was repeated multiple times for each metal combination. The selectivity and chlorobenzene conversion for each sample are shown below in Tables 3 and 4.

Example 1

Copper:Nickel

Samples 1 and 2 demonstrated that a copper:nickel metal combination used in the method described herein produced a reaction product with a selectivity that favored the formation of Si-Ph containing species. It also demonstrated that the amount of copper had an effect on both the product selectivity and the PhCl conversion.

Example 2

Copper:Iron

Samples 3 and 4 demonstrated that a copper:iron metal combination used in the method described herein produced a reaction product with selectivities that favored the formation of Si-Ph containing species. It also demonstrates that the amount of copper on the catalyst had an effect on both the product selectivity and the PhCl conversion.

Example 3

Copper:Palladium

Samples 5 and 6 demonstrated that a copper:palladium metal combination used in the method described herein produced a reaction product with a selectivity that favored the formation of Si-Ph containing species. It also demonstrated that the amount of copper on the catalyst had an effect on both the product selectivity and the PhCl conversion. These samples also produced lower levels of $PhSiCl_3$ than the Samples with Cu:Ni and Cu:Fe metal combinations, but these samples converted the majority of the PhCl.

Example 4

Copper:Cobalt

Sample 7 demonstrated that a copper:cobalt metal combination used in the method described herein produced a reaction product with a selectivity that favored the Si-Ph containing species.

Example-5

Copper:Chromium

Sample 8 demonstrated that a copper:chromium metal combination used in the method described herein produced a reaction product with a selectivity that favored the Si-Ph species.

Example-6

Copper:Manganese

Sample 9 demonstrated that a copper:manganese metal combination used in the method described herein produced a reaction product with selectivity that favored formation of Si-Ph species.

Example-7

Copper:Silver

Sample 10 demonstrated that a copper:silver metal combination used in the method described herein produced a reaction product with selectivity that favored the Si-Ph species. Table 9.

Example 8

Copper:Nickel:Palladium

Samples 11 and 12 demonstrated that a copper:nickel:palladium metal combination used in the method described herein produced a reaction product with selectivity that favored the formation of Si-Ph containing species. It also produced those Si-Ph containing species with a greater than 25% conversion of PhCl. The use of Ar as the carrier gas for the PhCl in Sample 12 significantly impacted the reaction product content with more Si-Ph containing phenyl-functional being produced than in Sample 11, in which $H_2$ was used as the carrier gas for the PhCl in step (2).

Example 9

Copper:Nickel:Palladium

Samples 13, 14, and 15 demonstrated that the amount of palladium in the copper-nickel-palladium metal combination had an effect on both the product selectivity and PhCl conversion. As the palladium amount decreased, the amount of $PhHSiCl_2$ increased and the PhCl conversion decreased. In the trial with Sample 15, which had the lowest amount of palladium of samples 13, 14, and 15, the amounts of $HSiCl_3$ and $SiCl_4$ in the reaction product significantly increased.

Example-10

Copper:Iron:Palladium

Sample 16 demonstrated that a copper:iron:palladium metal combination when used in the method described herein produced a reaction product with selectivity that favored the formation of Si-Ph containing species.

Example-11

Copper:Gold:Magnesium

Sample 17 demonstrated that a copper:gold:magnesium metal combination used in the method described herein produced a reaction product with selectivity that favored the formation of Si-Ph containing species.

TABLE 3

| | Selectivity of each compound in the reaction products prepared using Samples from Table 1 (%) | | | | | | | | | | | | | | | | |
|---|---|---|---|---|---|---|---|---|---|---|---|---|---|---|---|---|---|
| | Sample | | | | | | | | | | | | | | | | |
| Compound | 1 | 2 | 3 | 4 | 5 | 6 | 7 | 8 | 9 | 10 | 11 | 12 | 13 | 14 | 15 | 16 | 17* |
| Benzene | 38.92 | 50.67 | 30.24 | 56.39 | 74.76 | 44.15 | 67.31 | 71.97 | 78.15 | 60.94 | 42.39 | 17.53 | 21.05 | 13.87 | 22.18 | 21.30 | 40.10 |
| $HSiCl_3$ | 1.76 | 6.02 | 1.33 | 6.46 | 2.68 | 1.58 | 1.98 | 5.81 | 5.12 | 4.88 | 1.31 | 0.05 | 0.38 | 0.39 | 3.50 | 1.69 | 5.07 |
| $Ph_2SiCl_2$ | 0.00 | 0.00 | 0.00 | 0.00 | 0.00 | 0.00 | 0.00 | 0.00 | 0.00 | 0.00 | 5.43 | 7.80 | 7.66 | 7.43 | 5.99 | 22.84 | 0.00 |
| $SiCl_4$ | 2.26 | 5.42 | 1.38 | 7.44 | 9.28 | 1.19 | 7.69 | 3.01 | 7.84 | 17.24 | 1.41 | 1.23 | 1.41 | 1.18 | 3.86 | 1.78 | 5.26 |
| $PhHSiCl_2$ | 1.49 | 0.67 | 2.88 | 2.43 | 0.18 | 4.97 | 0.51 | 3.85 | 0.43 | 0.00 | 0.79 | 0.23 | 0.53 | 2.08 | 3.79 | 3.25 | 2.07 |
| $PhSiCl_3$ | 55.56 | 37.21 | 64.17 | 27.27 | 13.10 | 48.10 | 22.50 | 15.36 | 8.46 | 16.94 | 46.93 | 71.25 | 67.75 | 73.79 | 55.62 | 41.42 | 47.50 |

TABLE 4

| | Sample | | | | | | | | | | | | | | | | |
|---|---|---|---|---|---|---|---|---|---|---|---|---|---|---|---|---|---|
| | 1 | 2 | 3 | 4 | 5 | 6 | 7 | 8 | 9 | 10 | 11 | 12 | 13 | 14 | 15 | 16 | 17 |
| PhCl Conversion (%) | 26.62 | 7.99 | 15.15 | 9.16 | 90.22 | 9.87 | 21.84 | 5.74 | 6.41 | 5.33 | 26.17 | 36.65 | 36.77 | 25.43 | 14.76 | 18.01 | 1.74 |

For Samples 1-9, selectivities and PhCl conversion were the average of cycles 1-3.

For samples 10 and 17, the selectivities and PhCl conversion were from one cycle.

For samples 11-16, selectivities and PhCl conversion were the average of cycles 3-5.

*In this example, 0.75 g of the metal combination was used instead of 0.5 g.

For each of samples 1-11 and 17, in step (2) of the method where chlorobenzene was added to the reactor, the carrier gas was $H_2$.

For each of samples 12-16, in step (2) of the method where chlorobenzene was added to the reactor, the carrier gas was Ar.

The examples above show that in certain embodiments, the method provides a benefit in selectivity to produce more aryl-functional silanes (e.g., phenyl, chlorosilanes) in the reaction product. Higher amounts of one or more of $Ph_2SiCl_2$, $PhHSiCl_2$ and $PhSiCl_3$ indicate favorable selectivity to a desired reaction product. The method may provide the benefit of reduced amounts of unreacted halosilane and/or aryl halide (e.g., $SiCl_4$ and chlorobenzene) in the reaction product as compared to a method in which is used a different metal from the metal combination described herein for ingredient (B). The method may provide the benefit provide for reduced amounts of side product (e.g., benzene) production. The invention and advantages are not limited to solutions of the aforementioned problems or to the above benefits. Certain embodiments of this invention may independently solve additional problems and/or have benefits. Certain embodiments of this invention may have one, or one or more, but not all of the aforementioned benefits and still be within the scope of the invention set forth in the claims.

The disclosure of ranges includes the range itself and also anything subsumed therein, as well as endpoints. For example, disclosure of a range of >0 to 4 includes not only the range of 2 to 4, but also 2.1, 2.3, 3.4, 3.5, and 4 individually, as well as any other number subsumed in the range. Furthermore, disclosure of a range of, for example, >0 to 4 includes the subsets of, for example, 2.1 to 3.5, 2.3 to 3.4, 2.6 to 3.7, and 3.8 to 4, as well as any other subset subsumed in the range.

With respect to any Markush groups relied upon herein for describing particular features or aspects of various embodiments, it is to be appreciated that different, special, and/or unexpected results may be obtained from each member of the respective Markush group independent from all other Markush members. Each member of a Markush group may be relied upon individually and or in combination with any other member or members of the group, and each member provides adequate support for specific embodiments within the scope of the appended claims. For example, disclosure of the Markush group: $PhSiCl_3$, $Ph_2SiCl_2$, $Ph_3SiCl$, $PhSiBr_3$, $Ph_2SiBr_2$, $Ph_3SiBr$, $PhSiI_3$, $Ph_2SiI_2$, and $Ph_3SiI$, and combinations of two or more of $PhSiCl_3$, $Ph_2SiCl_2$, $Ph_3SiCl$, $PhSiBr_3$, $Ph_2SiBr_2$, $Ph_3SiBr$, $PhSiI_3$, $Ph_2SiI_2$, and $Ph_3SiI$ includes the member $PhSiCl_3$ individually, the subgroup $PhSiCl_3$ and $Ph_2SiCl_2$, and any other individual member and subgroup subsumed therein.

It is also to be understood that any ranges and subranges relied upon in describing various embodiments of the present disclosure independently and collectively fall within the scope of the appended claims, and are understood to describe and contemplate all ranges including whole and/or fractional values therein, even if such values are not expressly written herein. The enumerated ranges and subranges sufficiently describe and enable various embodiments of the present disclosure, and such ranges and subranges may be further delineated into relevant halves, thirds, quarters, fifths, and so on. As just one example, a range "of 500 to 1000" may be further delineated into a lower third, i.e., from 500 to 666, a middle third, i.e., from 667 to 833, and an upper third, i.e., from 834 to 1000, which individually and collectively are within the scope of the appended claims, and may be relied upon individually and/or collectively and provide adequate support for specific embodiments within the scope of the appended claims. In addition, with respect to the language which defines or modifies a range, such as "at least," "greater than," "less than," "no more than," and the like, it is to be understood that such language includes subranges and/or an upper or lower limit. As another example, a range of "at least 0.1%" inherently includes a subrange from 0.1% to 35%, a subrange from 10% to 25%, a subrange from 23% to 30%, and so on, and each subrange may be relied upon individually and/or collectively and provides adequate support for specific embodiments within the scope of the appended claims. Finally, an individual number within a disclosed range may be relied upon and provides adequate support for specific embodiments within the scope of the appended claims. For example, a range of ">0 to 4" includes various individual integers, such as 0 or 3, as well as individual numbers including a decimal point (or fraction), such as 2.1, which may be relied upon and provide adequate support for specific embodiments within the scope of the appended claims.

The subject matter of all combinations of independent and dependent claims, both singly and multiply dependent, is expressly contemplated but is not described in detail for the sake of brevity. The disclosure has been described in an illustrative manner, and it is to be understood that the terminology which has been used is intended to be in the nature of words of description rather than of limitation. Many modifications and variations of the present disclosure are possible in light of the above teachings, and the disclosure may be practiced otherwise than as specifically described.

The invention claimed is:

1. A method for preparing a reaction product comprising an aryl-functional silane comprises sequential steps (1) and (2), where:
   step (1) is contacting, under silicon deposition conditions
      (A) an ingredient comprising (I) a halosilane of formula $H_aSiX_{(4-a)}$, where each X is independently a halogen atom, and 0<a<1; and optionally (II) $H_2$, with the proviso that when a=0, then the hydrogen is present; and
      (B) a metal combination comprising copper and at least one other metal, where the at least one other metal is selected from the group consisting of cobalt, chromium, iron, manganese, nickel, palladium, and silver; thereby forming a silicon alloy catalyst comprising silicon, copper and the at least one other metal; and
   step (2) is contacting the silicon alloy catalyst and (C) a reactant comprising an aryl halide under silicon etching conditions; thereby forming the reaction product, where the reaction product comprises the aryl-functional silane and a spent catalyst;
   where the method may optionally further comprise step (3) and step (4), where
   step (3) is contacting, under silicon deposition conditions, an additional ingredient comprising (I) an additional halosilane of formula $H_aSiX_{(4-a)}$ and optionally (II) additional $H_2$; thereby re-forming the silicon alloy catalyst, and step (4) is contacting the silicon alloy catalyst re-formed in step (3) with an additional reactant comprising an additional aryl halide; thereby forming an additional amount of the reaction product, where the reaction product comprises the aryl-functional silane and the spent catalyst; and where the method, when further comprising steps (3) and (4), optionally further comprises step (5), where step (5) is repeating steps (3) and (4) at least one time; and where the method optionally further comprises step (6), where step (6) is recovering the aryl-functional silane after step (2), and/or when present, step (4), and/or step (5).

2. The method of claim 1, further comprising one or more additional steps, where the one or more steps are selected from:

purging and/or treating the metal combination, before contacting the metal combination with the ingredient comprising the halosilane in step (1); and/or purging and/or treating the silicon alloy catalyst, before contacting the silicon alloy catalyst with the reactant comprising the aryl halide in step (2); and/or purging and/or treating, the spent reactant before contacting the spent reactant with the additional ingredient in step (3); and/or purging and/or treating the reactant re-formed in step (3), before contacting the reactant re-formed in step (3) with the additional reactant in step (4); and/or purging and/or treating the additional spent reactant.

3. The method of claim 1, where a mole ratio of the $H_2$ to the halosilane ranges from 20:1 to 1:1.

4. The method of claim 1, where the at least one other metal comprises palladium.

5. The method of claim 1, where the at least one other metal comprises nickel.

6. The method of claim 5, where the at least one other metal further comprises palladium.

7. The method of claim 1, where the at least one other metal comprises iron.

8. The method of claim 7, where the at least one other metal comprises palladium.

9. The method of claim 1, where one of conditions (A) to (D) is satisfied:

(A) the at least one other metal comprises silver, or
(B) the at least one other metal comprises cobalt, or
(C) the at least one other metal comprises chromium, or
(D) the at least one other metal comprises manganese.

10. The method of claim 1, where the metal combination is provided on a support.

11. The method of claim 1, where step (1) is performed at a first temperature from 500° C. to 1000° C., and step (2) is performed at a second temperature from 100° C. to 600° C., with the proviso that the second temperature is lower than the first temperature.

12. The method of claim 1, where the halosilane (I) is silicon tetrachloride.

13. The method of claim 1, where the aryl halide is chlorobenzene.

14. The method of claim 1, where the aryl functional silane comprises one or more of $PhSiCl_3$, $Ph_2SiCl_2$, and $PhHSiCl_2$.

15. The method of claim 1, where step (2) is performed in the absence of hydrogen.

* * * * *